US010422797B2

(12) United States Patent
Kraus et al.

(10) Patent No.: US 10,422,797 B2
(45) Date of Patent: Sep. 24, 2019

(54) ELECTROCHEMILUMINESCENCE METHOD OF DETECTING AN ANALYTE IN A LIQUID SAMPLE AND ANALYSIS SYSTEM

(71) Applicants: Roche Diagnostics Operations, Inc., Indianapolis, IN (US); Hitachi High-Technologies Corporation, Minato-ku (JP)

(72) Inventors: Ralf Kraus, Peissenberg (DE); Oliver Larbolette, Penzberg (DE); Friedrich Staebler, Peissenberg (DE); Yoshihiro Yamashita, Tokyo (JP); Yukinori Sakashita, Tokyo (JP); Shinya Matsuoka, Tokyo (JP); Michihiro Saito, Tokyo (JP); Taku Sakazume, Tokyo (JP); Katsuaki Takahashi, Tokyo (JP)

(73) Assignees: ROCHE DIAGNOSTICS OPERATIONS, INC., Indianapolis, IN (US); HITACHI HIGH-TECHNOLOGIES CORPORATION, Tokyo (JP)

( * ) Notice: Subject to any disclaimer, the term of this patent is extended or adjusted under 35 U.S.C. 154(b) by 686 days.

(21) Appl. No.: 14/968,118

(22) Filed: Dec. 14, 2015

(65) Prior Publication Data
US 2016/0097765 A1 Apr. 7, 2016

Related U.S. Application Data

(63) Continuation of application No. PCT/EP2014/060149, filed on May 16, 2014.

(30) Foreign Application Priority Data

Jun. 19, 2013 (EP) .................................... 13172826

(51) Int. Cl.
| | |
|---|---|
| *G01N 33/543* | (2006.01) |
| *G01N 21/66* | (2006.01) |
| *G01N 21/76* | (2006.01) |
| *G01N 33/58* | (2006.01) |
| *G01N 35/00* | (2006.01) |
| *G01N 21/69* | (2006.01) |

(52) U.S. Cl.
CPC ......... *G01N 33/5438* (2013.01); *G01N 21/66* (2013.01); *G01N 21/69* (2013.01); *G01N 21/76* (2013.01); *G01N 33/54326* (2013.01); *G01N 33/54393* (2013.01); *G01N 33/582* (2013.01); *G01N 35/0098* (2013.01); *G01N 2035/00534* (2013.01); *G01N 2201/12* (2013.01)

(58) Field of Classification Search
None
See application file for complete search history.

(56) References Cited

U.S. PATENT DOCUMENTS

| | | | |
|---|---|---|---|
| 5,238,808 A | 8/1993 | Bard et al. | |
| 5,705,402 A * | 1/1998 | Leland ................. | C12Q 1/6825 436/518 |
| 5,779,976 A | 7/1998 | Leland et al. | |
| 6,599,473 B1 | 7/2003 | Egger et al. | |
| 6,673,533 B1 | 1/2004 | Wohlstadter et al. | |
| 6,881,536 B1 | 4/2005 | Shah et al. | |
| 6,994,971 B1 * | 2/2006 | Straume ................ | C12Q 1/6816 435/6.16 |
| 7,517,457 B2 * | 4/2009 | Siddiqi ................ | B01F 13/0809 209/217 |
| 2002/0077588 A1 * | 6/2002 | Schneider ............. | A61M 5/007 604/82 |
| 2005/0034842 A1 * | 2/2005 | Huber ................... | B01L 3/0241 165/80.4 |
| 2006/0110296 A1 * | 5/2006 | Tajima ................. | G01N 35/025 422/400 |
| 2006/0204997 A1 * | 9/2006 | Macioszek ........... | C12Q 1/6851 435/6.11 |
| 2009/0026373 A1 * | 1/2009 | Mertens ................ | B30B 11/005 250/339.07 |
| 2011/0020949 A1 * | 1/2011 | Sugiyama ............... | B01F 7/161 436/174 |

FOREIGN PATENT DOCUMENTS

| | | |
|---|---|---|
| CN | 10266949 A | 5/2011 |
| CN | 102066934 A | 5/2011 |
| CN | 102818907 A | 12/2012 |
| JP | H11-142414 A | 5/1999 |
| JP | 2010-249661 A | 11/2010 |
| WO | 1986002734 A1 | 5/1986 |

(Continued)

OTHER PUBLICATIONS

Office Action in China Patent Application 201470028847.9, filed May 16, 2014, dated Dec. 15, 2017.

(Continued)

*Primary Examiner* — Bao Thuy L Nguyen
*Assistant Examiner* — Ellen J Marcsisin
(74) *Attorney, Agent, or Firm* — Woodard, Emhardt, Henry, Reeves & Wagner, LLP (57) ABSTRACT

An electrochemiluminescence method of detecting an analyte in a liquid sample and a corresponding analysis system. An analyte in a liquid sample is detected by first providing a receptacle containing a fluid comprising protein coated magnetic microparticles to a stirring unit. Stirring of the fluid is necessary since the density of the microparticles is usually higher than the density of the buffer fluid. Thus the microparticles tend to deposit on the bottom of the receptacle leading to an aggregation of the microparticles because of weak interactions. To obtain representative measurements a homogeneous distribution of the microparticles in the buffer fluid is necessary to ensure a constant concentration of microparticles for each analysis cycle. It is further necessary to provide disaggregation of the microparticles, which is also realized by stirring the fluid. Stirring is conducted with a rotational frequency that is adapted to the amount of fluid to be stirred.

14 Claims, 5 Drawing Sheets

(56) References Cited

FOREIGN PATENT DOCUMENTS

| WO | WO 1989/0105551 A1 | 11/1989 |
|----|--------------------|---------|
| WO | 2002/014539 A1     | 2/2002  |
| WO | 2006068935 A1      | 6/2006  |
| WO | 2013052318 A1      | 4/2013  |

OTHER PUBLICATIONS

International Search Report dated Jul. 31, 2014 in Application No. PCT/EP2014/060149, 5 pages.

* cited by examiner

ELECTROCHEMILUMINESCENCE METHOD OF DETECTING AN ANALYTE IN A LIQUID SAMPLE AND ANALYSIS SYSTEM

CROSS-REFERENCE TO RELATED APPLICATIONS

This application is a continuation of International Patent Application No. PCT/EP2014/060149, filed 16 May 2014, which claims the benefit of European Patent Application No. 13172826.3, filed 19 Jun. 2013, the disclosures of which are hereby incorporated by reference in their entirety.

TECHNICAL FIELD

The present disclosure relates to the field of medical technology and diagnostics and, in particular, to a method of detecting an analyte in a liquid sample by effecting luminescence, such as by using a luminescence immunoassay, and a respective analysis system.

BACKGROUND

Numerous methods and systems have been developed for the detection and quantitation of analytes of interest in biochemical and biological substances. Methods and systems that are capable of measuring trace amounts of microorganisms, pharmaceuticals, hormones, viruses, antibodies, nucleic acids and other proteins are of great value to researchers and clinicians.

A significant body of art has been developed based upon the well-known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a potentiostatically or galvanostatically controlled working electrode in order to trigger luminescence. In the proper chemical environment, such electrochemiluminescence is triggered by a voltage or current impressed on the working electrode at a particular time and in a particular manner. The light produced by the label is measured and indicates the presence or quantity of the analyte.

In accordance with electrochemiluminescence binding reaction analysis (ECL-BBA) a detectable complex is produced, whose concentration constitutes a measure of the analytic result sought. A marking substances (label) capable of effecting an ECL-reaction is coupled to a binding reagent specific for the analyte, e.g., an antibody. The species comprising the marking substance and the binding reagent is designated as a label conjugate.

When such a substance is subjected to a suitable electrical potential on a voltammetric working electrode, it emits light which can be measured photometrically. A second electrochemically active substance, designated as a co-react and, normalty contributes to this reaction. In practice, primarily a ruthenium complex (ruthenium-tris [bipyridyl]) is used as ECL-label in combination with TPA (tripropylamine) as co-reactand. The two electrochemically active substances are both oxidized upon voltage application to the electrode. Subsequent loss of a proton will turn the TPA into a strongly reducing species. The subsequent redox reaction brings the ECL-label into an excited state from which it returns to the ground state with the emission of a photon. The ECL-label reaction is preferably a circular reaction so that a single label molecule emits a plurality of photons after application of a voltage to the electrode.

The ECL-marked complex molecules characteristic for the analysis are fixed to magnetic microparticles (beads). In practice, magnetized polystyrene beads having a diameter of typically 2 to 3 micrometers are used. Fixing is effected by means of a pair of specific biochemical binding partners. The pair streptavidin biotin has turned out to be particularly advantageous. The beads are streptavidin-coated, to which a biotinylated antibody will bind.

The beads with the bound marked complex are introduced into the measuring cell of a measuring apparatus. The cell is equipped with electrodes which are necessary for generating the electrical field required for triggering the ECL-reaction. The beads are drawn onto the surface of the working electrode in the magnetic field of a magnet disposed below the working electrode. Since this typically occurs in flow-through cells with continuously flowing sample fluids, the magnetic deposition of the beads is designated as "capturing". An electric potential required for triggering the ECL-reaction is then applied to the working electrode and the resulting luminescence light is measured using a suitable optical detector. The intensity of the luminescence light is a measure for the concentration of the number of labeled antibodies coupled to the beads on the surface of the working electrode which, in turn, is a measure of the concentration of the analyte in the sample. A calibration allows calculation of the sought concentration from the measured luminescence signal.

A plurality of different variations of this type of ECL-BBA-method have been discussed and described in the literature.

SUMMARY

It is against the above background that the embodiments of the present disclosure provide certain unobvious advantages and advancements over the prior art. In particular, the inventors have recognized a need for improvements in luminescence methods for detecting an analyte in a liquid sample and an analysis system.

In accordance with one embodiment of the present disclosure, an electrochemiluminescence method of detecting an analyte in a liquid sample is provided, the method comprising: providing a receptacle containing a fluid comprising protein coated magnetic microparticles to a stirring unit; acquiring a signal being indicative of an amount of the fluid contained in the receptacle; determining a rotational frequency for the stirring unit dependent on the amount of fluid in the receptacle, the rotational frequency being proportional to the amount of fluid; stirring the fluid for a predefined period of time by applying the previously determined rotational frequency; taking a portion of the fluid containing the protein coated magnetic microparticles from the receptacle, thereby reducing the amount of the fluid contained in the receptacle; mixing a portion of the liquid sample with the portion of the fluid comprising the protein coated magnetic microparticles and with a marker; incubating the mixture comprising the analyte, the protein coated magnetic microparticles, and the marker in an incubator; transporting a portion of the mixture from the incubator to a measurement cell; applying a magnetic field to the measurement cell for magnetic adhesion of the protein coated magnetic microparticles to a working electrode of the measurement cell; applying an excitation energy for causing luminescence; measuring of the luminescence for acquisition of a measurement signal, and generating an output signal being indicative of the presence of the analyte in the liquid sample using the measurement signal.

In accordance with another embodiment of the disclosure, an electrochemiluminescence analysis system for detecting an analyte in a liquid sample is provided comprising: a stirring unit for stirring a fluid containing magnetic microparticles provided in a receptacle; a measuring unit being operable to generate a signal indicative of an amount of fluid in the receptacle; an extraction component for extracting a portion of the fluid containing the protein coated magnetic microparticles from the receptacle; an incubator for receiving a liquid comprising the analyte, the portion of magnetic microparticles and a marker for marking the analyte, the marker being capable of effecting luminescence upon application of excitation energy; a trigger component for applying the excitation energy for causing the luminescence; and an acquisition component for measuring the luminescence the acquisition unit being operable to provide a measurement signal. The analysis system further comprises a data processing unit configured to determine a rotational frequency for the stirring unit using the signal indicative of the amount of fluid in the receptacle, the rotational frequency being proportional to the amount of fluid; control the stirring unit to stir the fluid for a predefined period of time by applying the previously determined rotational frequency; and generate an output signal being indicative of the presence of the analyte in the liquid sample using the measurement signal.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

In some embodiments of the present disclosure an analyte in a liquid sample is detected by first providing a receptacle containing a fluid comprising protein coated magnetic microparticles to a stirring unit. Stirring of the fluid comprising protein coated magnetic microparticles is necessary since the density of the microparticles is usually higher than the density of the buffer fluid. Thus the microparticles tend to deposit on the bottom of the receptacle leading to an aggregation of the microparticles because of weak interactions. To obtain representative measurements a homogeneous distribution of the microparticles in the buffer fluid is necessary to ensure a constant concentration of microparticles for each analysis cycle. Besides homogenization it is further necessary to provide disaggregation of the microparticles as well, which is also realized by stirring the fluid comprising the microparticles.

In this context the term "to stir" is to be understood as "to mix something by making circular movements in it using an object suitable for mixing".

Stirring the fluid comprising protein coated microparticles has several advantages over other ways and means to disaggregate the microparticles. For example, the microparticles may be disaggregated using supersonic sound. Supersonic sound may however cause damage of the protein coating of the microparticles. Another possibility may be vortex mixing of the fluid containing the microparticles, which may however cause severe foam generation that is detrimental for representative measurements as discussed below. A third possibility may be the use of extensional flow caused by a piston pipettor. The use of a piston pipettor for mixing the fluid may however cause mechanical stress for the protein coated microparticles which may lead to damage of the coating.

To provide disaggregation of the microparticles a certain amount of energy dependent on the amount of fluid comprising the microparticles to be stirred has to be applied to the fluid. The amount of energy applied to the fluid during the stirring process depends on the rotational frequency of the stirrer and the amount of time during which the fluid is stirred.

In a next method step a signal being indicative of the amount of fluid contained in the receptacle is acquired. The signal may for example be acquired by reading an RFID tag of the receptacle or other memory or by measuring the filling level of the receptacle as described below. One may also weigh the receptacle containing the fluid and knowing the weight of the receptacle itself and the density of the fluid comprising the magnetic microparticles could determine the volume of the fluid contained in the receptacle.

Dependent on the previously determined amount of fluid contained in the receptacle a rotational frequency for the stirring unit is determined, for example by looking up a table comprising information on which rotational frequency to use for which amount of fluid. The applied rotational frequency should be high enough to provide for short time periods for stirring the fluid. However the rotational frequency should not be too high, because a too high rotational frequency might cause foam generation which in turn may lead to unwanted effects. For example, extraction of predefined and repeatable amounts of fluid may not be possible if the fluid is at least partially foamed.

After stirring the fluid for a predetermined period of time by applying the previously determined rotational frequency, a portion of the fluid containing the protein coated magnetic microparticles is taken from the receptacle, thereby reducing the amount of fluid contained in the receptacle. The portion of the fluid comprising the magnetic microparticles is then mixed with a portion of the liquid sample comprising the analyte and a marker, and the mixture is incubated in an incubator. A portion of the mixture is then transported to a measurement cell, where a magnetic field is applied for magnetic adhesion of the protein coated magnetic microparticles to a working electrode of the measurement cell.

After application of an excitation energy for causing luminescence the luminescence is measured for acquisition of a measurement signal. Using the measurement signal an output signal being indicative of the presence of the analyte in the liquid sample is generated.

An "analyte" as understood herein is a component of the liquid sample to be analyzed, e.g., molecules of various sizes, proteins, metabolites and the like.

A "liquid sample" as understood herein encompasses a biological sample such as any kind of tissue or body fluid having been derived from a human or any other organism. In particular, a biological sample can be a blood-, serum-, plasma-, urine-, cerebral-spinal fluid-, or saliva-sample, or any derivatives thereof.

The term "luminescence" as understood herein encompasses any kind of luminescence such as radiation-induced luminescence, chemiluminescence and electrochemiluminescence, in particular ECL-BBA.

The term "luminescence immunoassay" as understood herein encompasses any immunoassay that produces an optical signal, i.e., a luminescence signal that indicates the presence of a particular analyte in a liquid sample.

The method described above is configured so that individual analysis runs can be carried out with constant expenditure of time. During a series of analysis cycles the amount of fluid comprising the magnetic microparticles contained in a receptacle may change. Thus the amount of energy to be applied to the fluid during stirring has to be adapted to the amount of fluid contained in the receptacle. However, using the method steps described above the rotational frequency of the stirrer can be adapted to the amount of fluid to be stirred, such that the time for stirring can be held constant for each stirring process.

This facilitates the automation of the previously described analysis procedure. In most common analysis systems employing a stirring unit the rotational frequency of the stirrer is the same for each analysis cycle, irrespective of the amount of fluid to be stirred. Thus the rotational frequency of the stirrer has to be adapted such that even for a minimal amount of fluid contained in the receptacle no foam is generated by the stirring process. However if the receptacle contains a large amount of fluid stirring with the previously described low rotational frequency will consume considerably more time than stirring with a rotational frequency that has been adapted to the amount of fluid to be stirred and thus will slow down the analysis process.

In some embodiments acquiring a signal being indicative of the amount of fluid contained in the receptacle is conducted using a pipetting probe that is also used for extracting a portion of fluid from the receptacle. This may have the advantage that a signal being indicative of the amount of fluid contained in the receptacle may be generated while a portion of fluid is extracted from the receptacle. Thus, two method steps can be carried out simultaneously thereby reducing the expenditure of time of an analysis cycle.

In some embodiments the pipetting probe may comprise a capacitive sensor for acquiring a signal being indicative of the amount of fluid contained in the receptacle. For example, the capacitive sensor may be designed such that it responds to changes of the humidity of its environment. The capacitive sensor may be located at the tip of the pipetting probe such that a measurement signal of the capacitive sensor is produced once the tip of the pipetting probe comes into contact with the surface of the fluid contained in the receptacle. To obtain the filling level of the receptacle from the previously described measurement signal, one may for example lower the pipetting probe from a known starting height in predefined steps. After each step the voltage or any other indicator of the capacitive sensor is measured. Once the tip of the pipetting probe comes into contact with the fluid a value of the measured indicator will change. Since the starting height of the pipetting probe is known and the step size of the lowering process is known as well, one can easily determine the filling level of the receptacle.

In some embodiments determining the rotational frequency for the stirring unit may comprise providing a signal being indicative of the amount of fluid contained in the receptacle to a data processing unit. The data processing unit may for example comprise a table wherein the table comprises information on which rotational frequency to use for a certain amount of fluid contained in the receptacle. Even though it may be possible to calculate the values for such a table using the laws of physics and for example employing a numerical method, according to a typical embodiment the data may also be determined empirically. Once the data processing unit determined the rotational frequency to use by looking up the table, the data processing unit provides a second signal being indicative of the rotational frequency appropriate for the amount of fluid that has previously been determined.

In another aspect the present disclosure relates to an analysis system for detecting an analyte in a liquid sample.

In some embodiments the analysis system may comprise a stirring unit for stirring a fluid containing magnetic microparticles provided in a receptacle and a measuring unit being operable to generate a signal indicative of an amount of fluid in the receptacle. For extracting a portion of the fluid containing the protein coated magnetic microparticles from the receptacle, the analysis system may further comprise an extraction component. To initiate a transfer of the liquid comprising the analyte, the portion of magnetic microparticles and a marker for marking the analyte, the analysis system may further comprise an incubator. The marker for marking the analyte typically is capable of effecting luminescence upon application of excitation energy. To obtain a measurement signal the analysis system may further comprise a trigger component for applying the excitation energy for causing the luminescence and acquisition component for measuring the luminescence, the acquisition unit being configured/operable to provide a measurement signal and a data processing unit being adapted to determine an appropriate rotational frequency for the stirring unit using the signal indicative of the amount of fluid in the receptacle and to generate an output signal being indicative of the presence of the analyte in the liquid sample using the measurement signal.

In this case the term "adapted to" with reference to the data processing unit of the analysis system includes that the data processing unit is configured to carry out the described method steps.

It is understood that one or more of the aforementioned embodiments of the disclosure may be combined as long as the combined embodiments are not mutually exclusive.

In order that the embodiments of the present disclosure may be more readily understood, reference is made to the following examples, which are intended to illustrate the disclosure, but not limit the scope thereof.

Figure 1:
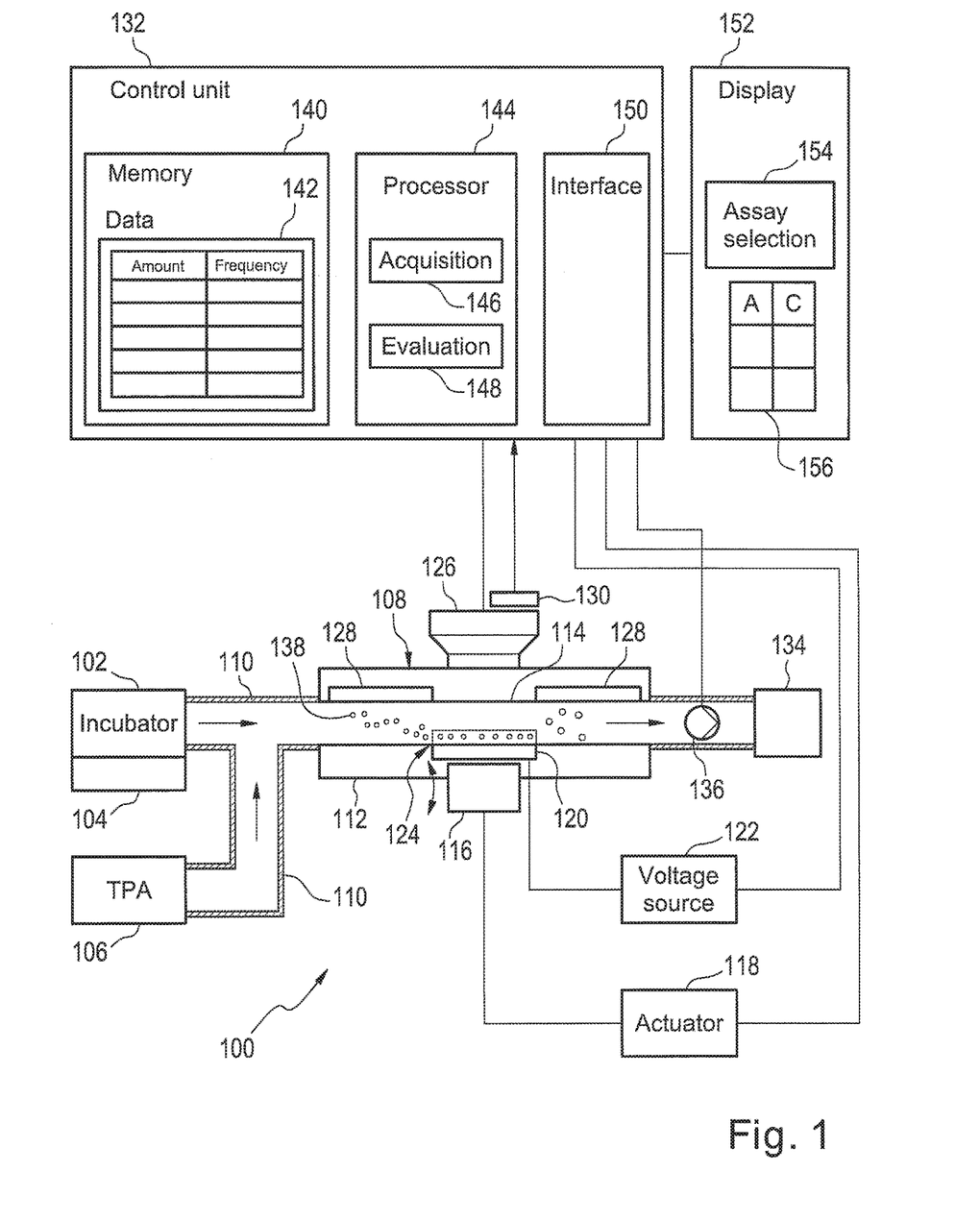
FIG. 1 is a block diagram of an analysis system in accordance with one embodiment of the disclosure.

FIG. 1 shows an analysis system 100 for detecting an analyte in a liquid sample. The analysis system 100 comprises an incubator 102 for receiving a liquid 104 that is a mixture of an aliquot of the liquid sample and a marker for marking the analyte, such as of a luminescence immunoassay.

The analysis system 100 comprises a reservoir 106 that contains the co-reactant of the electrochemical reaction causing the luminescence. The incubator 102 and the reservoir 106 are coupled to a measurement cell 108 of the analysis system by a pipe system 110 through which a portion of the liquid 104 and the co-reactant can flow into the measurement cell 108.

The measurement cell 108 comprises a cell body 112 that has a conduit 114 for receiving a portion of the liquid 104 and of the co-reactant through the pipe system 110. The measurement cell 108 has a magnetic component 116, such as a permanent magnet, for providing a magnetic field in the measurement cell. The magnetic component 116 may be coupled to an actuator 118 for rotating the magnetic component 116 to and from the conduit 114 in order to switch on or off the magnetic field within the conduit.

The magnetic component 116 is positioned below a working electrode 120 that is coupled to a voltage source 122. An excitation area 124 is formed in the conduit 114 within the magnetic field caused by the magnetic component 116 on the working electrode 120.

Luminescence that is caused in the excitation area 124 by the application of excitation energy, i.e., the application of a voltaic trigger pulse on the working electrode 120, is measured by means of an optical sensor, such as a photomultiplier 126. The optical sensor is sensitive within a certain frequency range such that it provides a measurement signal, such as a luminescence signal caused by autoluminescent molecules that may be present in the measurement cell, provided that the luminescence is within the sensor's frequency range.

The photomultiplier 126 is positioned opposite to the excitation area 124 over a window formed by counter electrodes 128 of the working electrode 120 through which the luminescence photons and any interfering photons caused by the excitation energy impinge on the photomultiplier 126. A resultant time resolved measurement signal 130 is provided from the photomultiplier 126 to a control unit 132 of the analysis system 100.

After a measurement has been performed the liquid contained within the conduit 114 is removed into a liquid waste container 134 and the measurement cell 108 is regenerated for a subsequent acquisition of a measurement signal.

The control unit 132 is coupled to the voltage source 122 in order to control the voltage source 122 to apply the trigger signal to the working electrode 120. The control unit 132 is also coupled to the actuator 118 for controlling the actuator 118 to switch on and off the magnetic field by moving the permanent magnet correspondingly.

Further, the control unit 132 may be coupled to a "sipper unit", i.e., a pump 136, for extracting a portion of the liquid 104 from the incubator 102 and a portion of the co-reactant from the reservoir 106 as well as for removing the liquid from the measurement cell 108 and regeneration of the measurement cell. In addition, the control unit 132 may be coupled to additional robotic components such as a pipetting station (cf., embodiment of FIG. 3).

The measurement cell 108 may be adapted for performing ECL-BBA using various luminescence immunoassays.

For example, the liquid 104 may contain a mixture of an aliquot of the liquid sample, streptavidin coated magnetic particles, biotinylated antibodies and ruthenylated antibodies to form a so-called "sandwich" whereas the co-reactant contained in the reservoir 106 is tripropylamine. Hence, magnetic particles 138 with a bound label flow into the conduit 114. The magnetic particles 138 are immobilized on the working electrode 120 when the magnetic field is switched on. Next, the trigger pulse is applied on the working electrode 120 to cause the electrochemiluminescence in accordance with the ECL-BBA technique.

Figure 3:
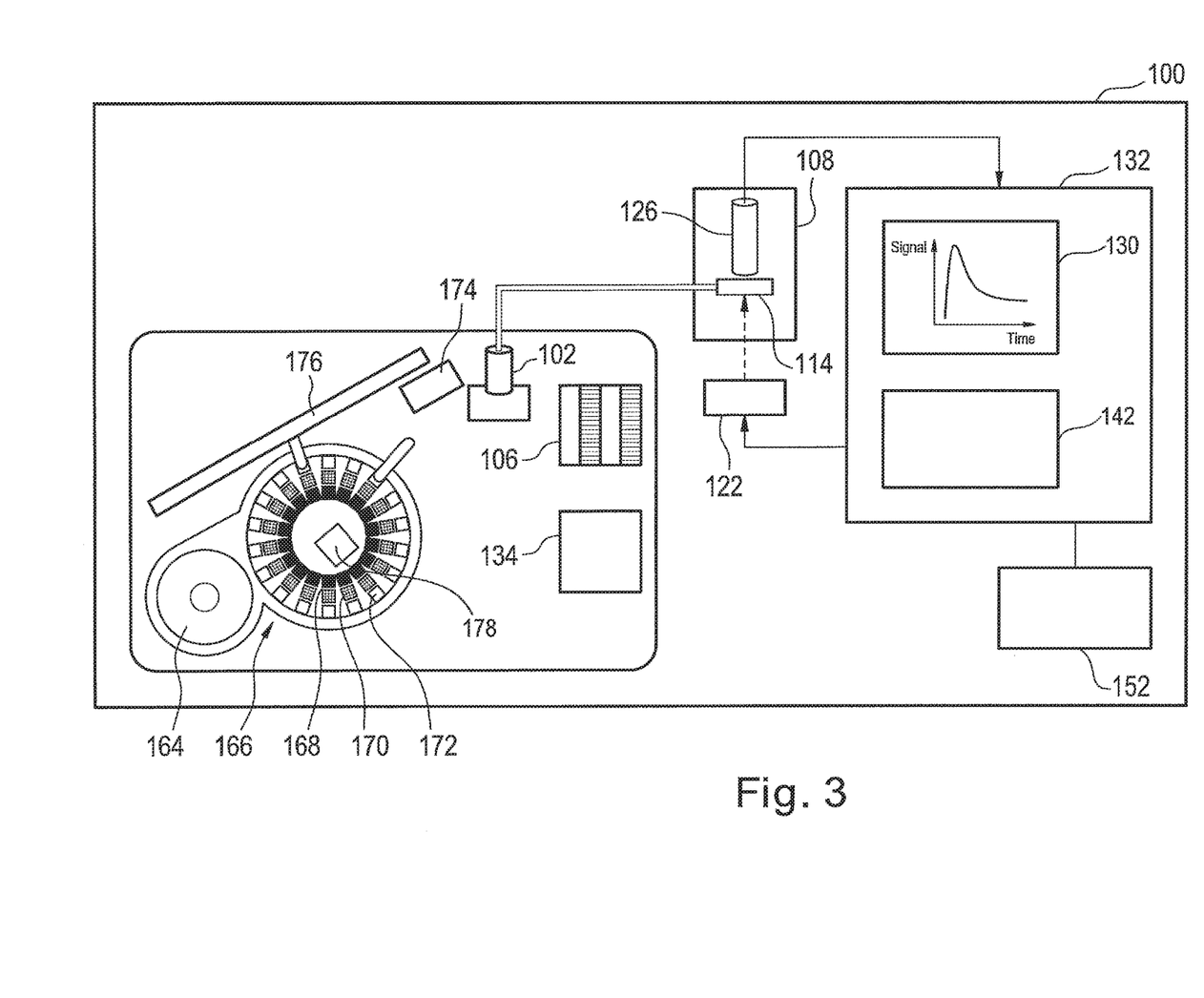
FIG. 3 is a block diagram of an analysis system comprising a robotic component in accordance with another embodiment of the disclosure.

The control unit 132 has an electronic memory 140 for storing data 142 that describes which rotational frequency for a stirring unit to use for a certain amount of fluid contained in a receptacle 168 (cf., FIG. 3). In the embodiment considered here the data 142 is stored in a lookup table or database table and will be discussed with reference to FIG. 3.

The control unit 132 has at least one electronic processor 144 for execution of program modules 146 and 148. Program module 146 is executed by the processor 144 for acquisition of the measurement signal 132 whereas the program module 148 is executed by the processor 144 for evaluation of the acquired measurement signal 132.

The control unit 132 has an interface 150 for coupling a display 152 or another human-machine-interface to the control unit 132. The interface 150 may be implemented as a graphical user interface for displaying a window 154 for a user's selection of one of the luminescence immunoassays supported by the analysis system 100 as well as a window 156 for displaying a result of the analysis.

The result of the analysis performed by the analysis system 100 may be output as tabular data as depicted in FIG. 1 wherein the column A indicates the analyte to be detected and the column C indicates the concentration of the analyte that has been detected.

In operation, a user selects one of the luminescence immunoassays supported by the analysis system 100 by entering a respective selection into the window 154. The analysis of the liquid sample is started by execution of the program module 146 such that the pump 136 is controlled to transport a portion of the liquid 104 and of the co-reactant into the conduit 114.

Next, the actuator 118 is controlled to flip the permanent magnet into a position such that its magnetic field is applied to the conduit 114 for immobilization of the magnetic particles with their bound labels on the working electrode 120. Next, the voltage source 122 is controlled to apply the trigger pulse onto the working electrode for excitation of the luminescence such that the measurement signal 130 results.

The measurement signal 130 is acquired by sampling the output of the photomultiplier 126 over a given period of time, such as 2 seconds after application of the trigger pulse by the voltage source 122, for time-resolved measuring of the luminescence.

The data samples that constitute the measurement signal 130 are stored within the memory 140 of the control unit 132 and the program module 148 is started for evaluation of the acquired measurement signal 130. By execution of the program module 148 the concentration C of the analyte, if any, in the liquid is determined by means of the measurement signal 130.

Next, the pump 136 is controlled by the control unit 132 for removing the liquid from the conduit 114 and regeneration of the measurement cell 108.

Figure 2:
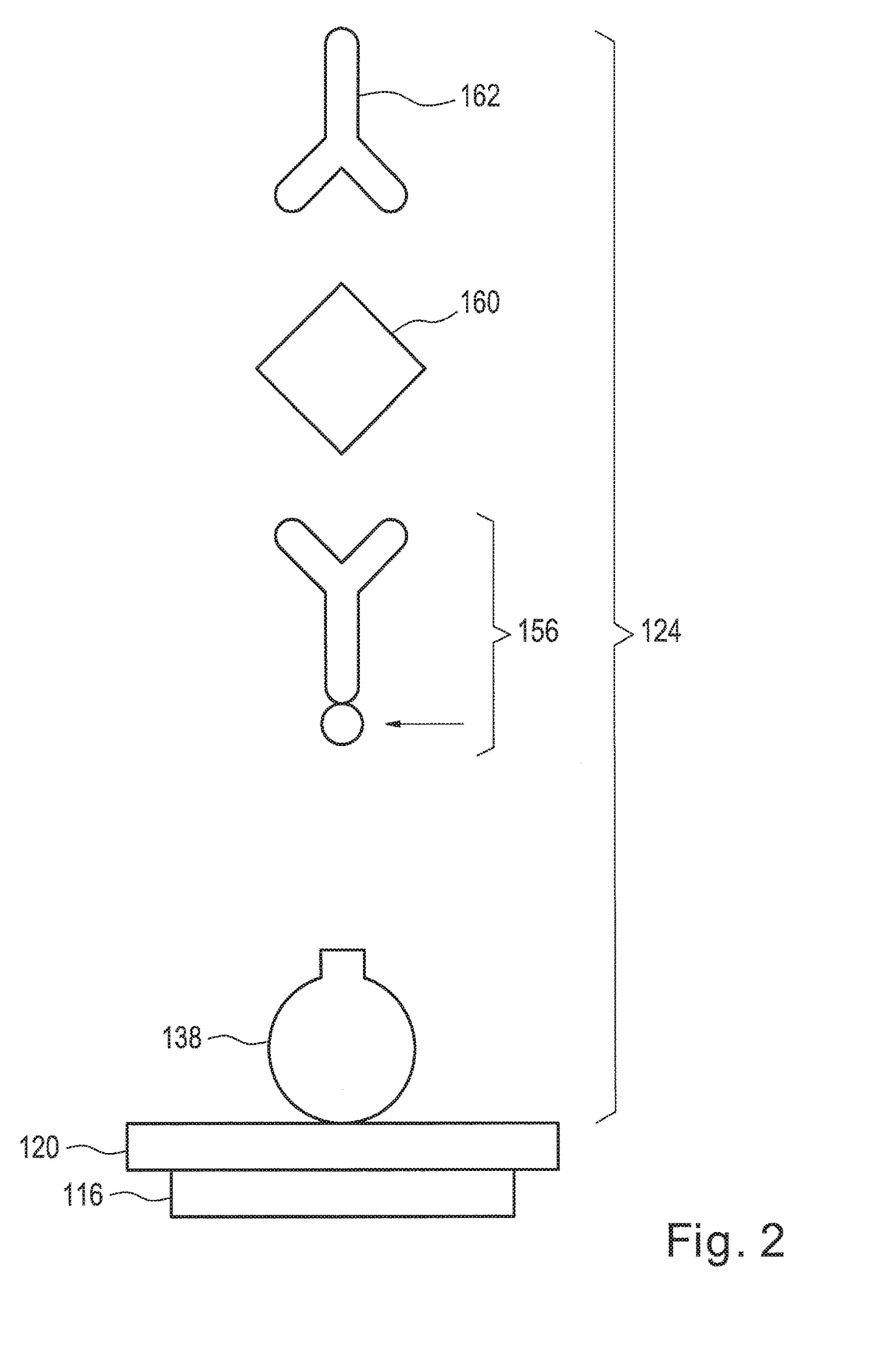
FIG. 2 is a diagram illustrating the ECL-BBA technique in accordance with one embodiment of the disclosure.

FIG. 2 is illustrative of the "sandwich" that is formed within the incubator 102 and to which a trigger pulse is applied within the excitation area 124 on the working electrode 120. In the embodiment considered here each of the magnetic particles 138 has a diameter of about 2.8 micrometers. The magnetic particle 138 is bound to a biotinylated antibody 158 of the immunoassay that is chosen depending on the analyte 160 to be detected. A ruthenium complex (ruthenium-tris [bipyridyl]) bound to an antibody 162 that is chosen depending on the analyte 160 is utilized as a luminescent label in the embodiment considered here.

Upon application of the voltaic trigger pulse an electrochemical reaction is induced with the tripropylamine in accordance with the ECL-BBA technique such that luminescence is caused.

FIG. 3 shows a further embodiment of an analysis system 100. The analysis system 100 has a rotor 164 for receiving receptacles, such as sample tubes, where each sample tube contains a liquid sample. The rotor 164 may hold a number of sample tubes for providing random access to a pipettor 176.

The analysis system 100 has a second rotor 166 for receiving receptacles 168 containing streptavidin-coated magnetic microparticles, receptacles 170 containing biotinylated antibodies and receptacles 172 containing ruthenylated antibodies. The second rotor may be implemented as a reagent disk as shown in FIG. 3 for providing access of the pipettor 176 to the various reagents contained in the receptacles 168, 170 and 172. The second rotor 166 further comprises a stirring unit 178 that may for example be mounted in the center of the reagent disk such that the stirring unit 178 can provide disaggregation of the streptavidin-coated magnetic microparticles contained in the receptacle 168 by stirring the fluid contained in receptacle 168 (cf., FIGS. 4, 5). Control unit 132 controls the stirring unit 178 thereby causing the stirring unit 178 to stir the fluid contained in receptacle 168 with a rotational frequency that is adapted to the amount of fluid contained in the receptacle 168.

The analysis system 100 has a robotic component for providing a mixture to the incubator 102. In the embodiment considered here the robotic component is controlled by the control unit 132 and comprises a pipetting station 174 having the pipettor 176.

In operation, the control unit 132 determines rotational frequency for the stirring unit 178 to stir the fluid in receptacle 168. The rotational frequency may for example be determined by the control unit 132 by determining the amount of fluid contained in receptacle 168 and looking up a table comprising information on which rotational frequency to use for which amount of fluid. The amount of fluid contained in the receptacle 168 may for example be determined from the filling level of the receptacle 168 as described below.

Once an appropriate rotational frequency for the stirring unit 178 has been determined the stirring unit is controlled by the control unit 132 to stir the fluid in receptacle 168 with the determined rotational frequency for a predetermined amount of time.

The control unit 132 then controls the pipettor 176 to extract an aliquot of the liquid sample from one of the sample tubes that are held by the rotor 164 and to extract portions of the streptavidin-coated magnetic particles, the biotinylated antibodies and the ruthenylated antibodies from the receptacles 168, 170 and 172, respectively, in order to provide the mixture that is then put into the incubator 102 for incubation during a predetermined amount of time, such as 9 to 27 min.

Upon extracting a portion of the streptavidin-coated magnetic microparticles the amount of fluid contained in receptacle 168 may be determined. For example the pipettor may comprise capacitive means suitable for providing a measurement signal once the pipette tip touches the surface of the fluid contained in receptacle 168. If the starting height of the pipette tip is known and the change of height caused by a vertical actuator is logged during lowering, the liquid level of receptacle 168 can be determined from the measurement signal of the capacitive means and the corresponding height of the pipette tip.

The control unit 132 controls the "sipper", e.g., the pump 136 (cf., FIG. 1), such that the liquid mixture flows from the incubator 102 into the conduit 114 of the measurement cell 108 together with the co-reactant, i.e., tripropylamine. Next, the control unit 132 controls the actuator 118, (cf., FIG. 1) to switch on the magnetic field and then the voltage source 122 to apply the voltaic trigger pulse.

The resultant measurement signal 130 is acquired by the control unit 132 by sampling the output of the photomultiplier 126.

Figure 4:
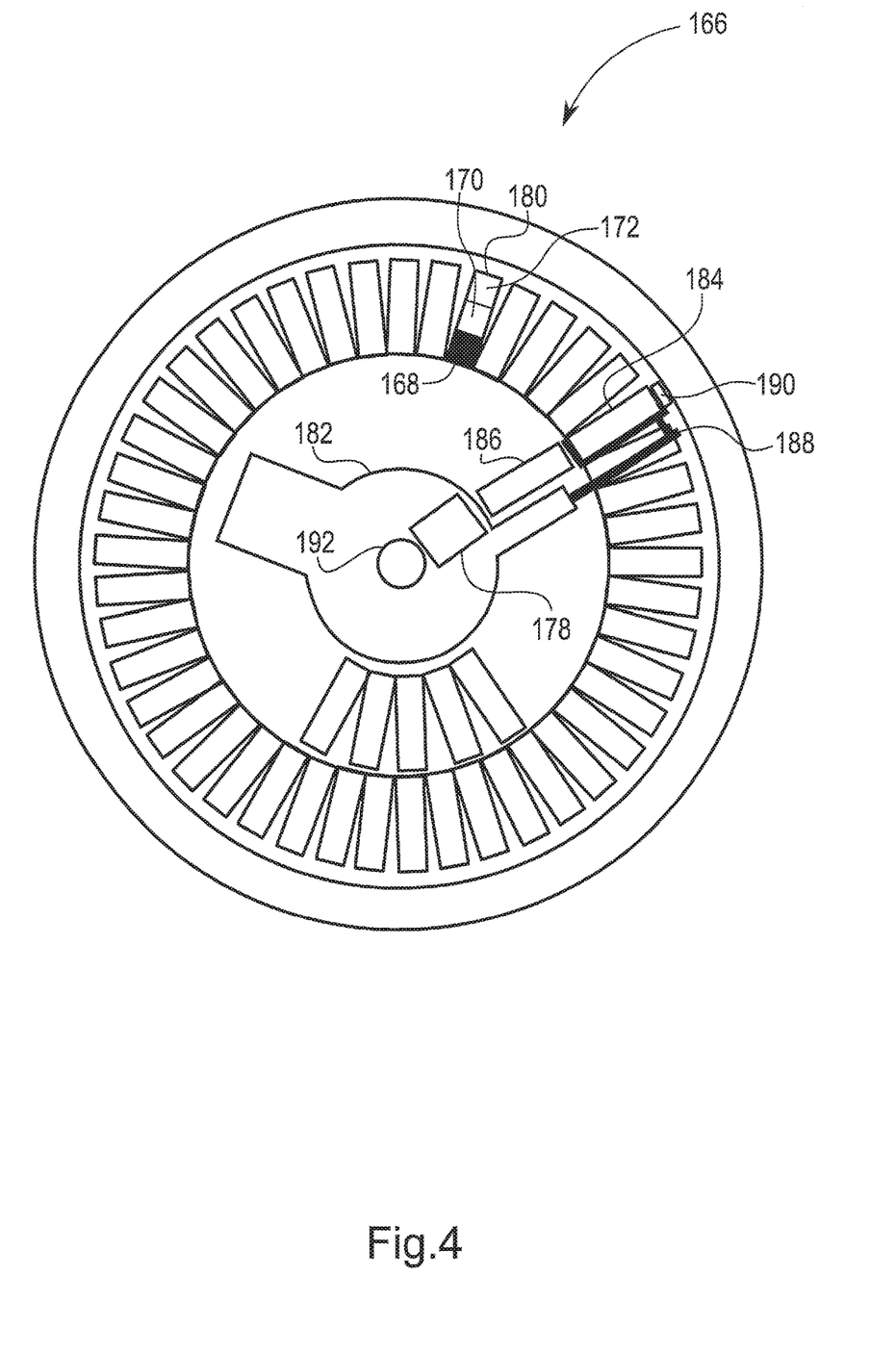
FIG. 4 is a block diagram of a rotor for receiving receptacles in accordance with an embodiment of the disclosure.

FIG. 4 shows a rotor 166 for use in an analysis system as described with reference to FIG. 3. The rotor 166 is designed for receiving e-packs 180 comprising the receptacles 168 containing streptavidin-coated magnetic microparticles, the receptacles 170 containing biotinylated antibodies and the receptacles 172 containing ruthenylated antibodies. The e-packs 180 are arranged to form a ring that can be rotated clockwise or counterclockwise. The receptacle 168 containing the streptavidin-coated magnetic microparticles is located at the innermost position of an e-pack 180.

Rotor 166 further comprises an e-pack shifter 182 for moving e-packs 180 from an outer position 184 to an inner position 186. The e-pack shifter 182 may for example employ a grappler 188 for moving the e-packs 180. For proper identification of a selected e-pack 180 the e-packs 180 are equipped with RFID tags that can be read or written by the RFID reader/writer 190.

E-pack shifter 182 further comprises a stirring unit 178. The stirring unit 178 is located such that it may reach the innermost receptacle 168 containing streptavidincoated microparticles of the e-pack 180 in inner position 186 for stirring. In a central portion of the e-pack shifter 182 a cleaning station 192 for the stirring unit 178 is located.

In operation, an e-pack 180 may be selected for processing by rotating the ring of e-packs 180 until the e-pack 180 to be processed has been identified by the RFID reader/writer 190. The e-pack 180 is then moved from the outer position 184 to the inner position 186 by the grappler 188 of the e-pack shifter 182. The stirring unit 178 may then stir the fluid contained in the innermost receptacle 168 with a predetermined rotational frequency to provide sufficient disaggregation of the microparticles contained in the fluid.

The applied rotational frequency for the stirring unit 178 may for example be provided to the stirring unit 178 by the control unit 132 (not shown). For that purpose the control unit 132 may be coupled with the RFID reader/writer 190 for exchange of information on which e-pack 180 is currently in the inner position 186 for processing. The control unit 132 may then look up a table comprising information on the amount of fluid contained in the corresponding receptacle 168 and then may look up another table comprising information on which rotational frequency to use for the determined amount of fluid.

It is also possible to write information on the amount of fluid in receptacle 168 of an e-pack 180 to the corresponding RFID tag using the RFID reader/writer 190.

The control unit 132 then would simply have to read the information on the amount of fluid from the RFID tag using the RFID reader/writer 190 and look up a table comprising information on which rotational frequency to use for the determined amount of fluid. This would further have the advantage that the e-packs 180 could be transferred from one analysis system to another without losing the information on the amount of fluid in receptacle 168 of the e-packs 180.

Once the stirring process has ended, the pipettor 176 of the pipetting station 174 may extract portions of the streptavidin-coated magnetic particles, the biotinylated antibodies and the ruthenylated antibodies from the receptacles 168, 170 and 172, respectively, in order to provide the mixture that is then put into the incubator 102 for incubation. After the portions have been extracted the e-pack 180 may be moved from the inner position 186 to the outer position 184 by grappler 188 and another e-pack 180 may be selected by rotating the ring of e-packs 180.

Before a subsequent stirring process is started the stirring unit may be cleaned using the cleaning station 192. To allow the stirring unit 178 to reach both the sample tubes within the e-pack 180 in innermost position 186 and the cleaning station 192 the stirring unit may for example be pivot-mounted or mounted on a slide that can move the stirring unit from a mixing position to a cleaning position and vice versa.

Figure 5:
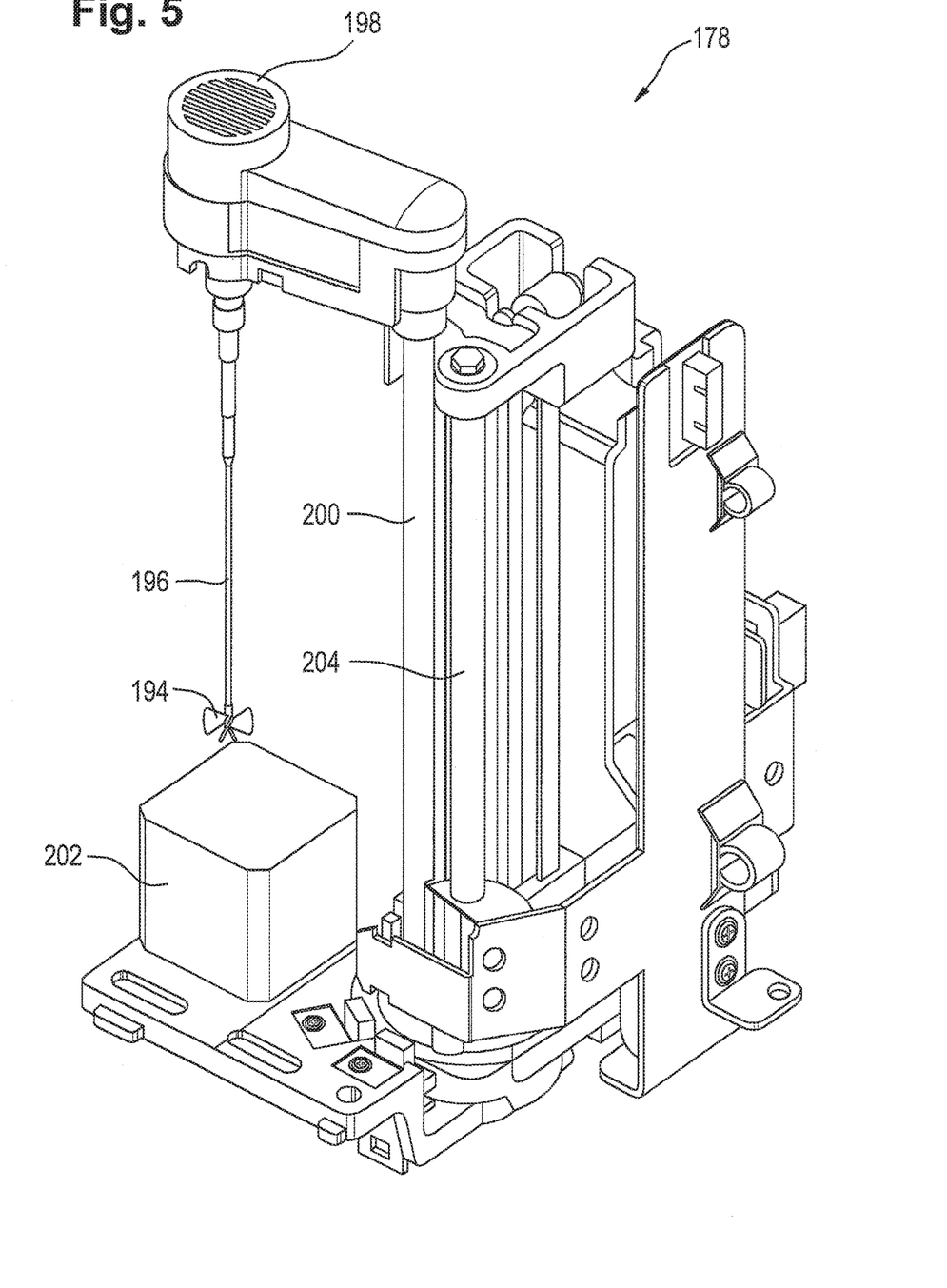
FIG. 5 is a schematic of a stirring unit in accordance with an embodiment of the disclosure.

FIG. 5 shows an exemplary embodiment of a stirring unit 178. The stirring unit 178 comprises a stirrer 194 mounted on a shaft 196 that is driven by a motor 198.

The assembly of motor 198, shaft 196 and stirrer 194 is mounted on a rod 200 such that the vertical position of the stirrer 194 can be varied. Block 202 below the stirrer 194 indicates the position of a receptacle containing a fluid to be stirred.

The assembly of rod 200, motor 198, shaft 196 and stirrer 194 is mounted on a pivotable socket that is driven by shaft 204. Thus it is possible to switch the stirring assembly between at least two positions: a first position in which the stirrer 194 is located above a receptacle containing a liquid to be stirred, and a second position in which the stirrer 194 and the shaft 196 may be cleaned, for example, by dipping stirrer 194 and shaft 196 into a cleaning liquid. Instead of mounting the stirring assembly on a pivotable socket the stirring assembly could also be mounted on a slide to switch between the stirring and the cleaning position.

In operation, a receptacle is moved below the stirrer 194, for example by the grappler 188 of the e-pack shifter 182 as described with reference to FIG. 4. Subsequently the stirring assembly comprising stirrer 194, shaft 196 and motor 198, is lowered until the stirrer 194 is completely immersed in the fluid. Then the motor 198 is controlled by a control unit 132 (not shown) to apply a rotational frequency to the stirrer 194 appropriate for disaggregating microparticles contained in the fluid. The fluid is then stirred for a predetermined amount of time with the predetermined amount rotational frequency to provide for sufficient disaggregation of the microparticles. Once the stirring process is completed the stirring assembly is raised, until the stirrer is located above the fluid at a sufficient height.

In a next step the shaft 204 may be operated to rotate the stirring assembly into a cleaning position in which the stirrer is located above a receptacle comprising a cleaning liquid. After lowering the stirring assembly until the stirring assembly is fully immersed in the cleaning fluid the motor 198 may again rotate the shaft 196 and the stirrer 194 thereby cleaning shaft 196 and stirrer 194. Upon raising the stirring assembly out of the cleaning liquid the stirring assembly may be rotated back to the stirring position such that the stirring unit 178 is ready for the next stirring procedure.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents. Numbered embodiments are presented below.

LIST OF REFERENCE NUMERALS

Analysis system 100
Incubator 102
Liquid 104
Reservoir 106
Measurement cell 108
A pipe system 110
Cell body 112
Conduit 114
Magnetic component 116
Actuator 118
Working electrode 120
Voltage source 122
Excitation area 124
Photomultiplier 126
Counter electrode 128
Measurement signal 130
Control unit 132
Container 134
Pump 136
Particle 138
Memory 140
Reference data 142
Processor 144
Program module 146

Program module 148
Interface 150
Display 152
Window 154
Window 156
Biotinylated antibody 158
Analyte 160
Ruthenylated antibody 162
Rotor 164
Rotor 166
Receptacles 168
Receptacles 170
Receptacles 172
Pipetting station 174
Pipettor 176
Stirring unit 178
E-pack 180
E-pack shifter 182
Outer position 184
Inner position 186
Grappler 188
RFID reader/writer 190
Cleaning station 192
Stirrer 194
Shaft 196
Motor 198
Rod 200
Block 202
Shaft 204

What is claimed is:

1. An electrochemiluminescence method of detecting an analyte in a liquid sample, the method comprising:
providing a receptacle containing a fluid comprising protein coated magnetic microparticles to a stirring unit,
acquiring a first signal indicative of the amount of the fluid contained in the receptacle,
determining based on the first signal a rotational frequency for the stirring unit dependent on the amount of fluid in the receptacle,
stirring the fluid for a period of time at the determined rotational frequency,
taking a portion of the fluid comprising the protein coated magnetic microparticles from the receptacle, thereby reducing the amount of the fluid contained in the receptacle,
mixing a portion of the liquid sample with the portion of the fluid comprising the protein coated magnetic microparticles and with a marker,
incubating the mixture comprising the analyte, the protein coated magnetic microparticles, and the marker in an incubator,
transporting a portion of the incubated mixture from the incubator to a measurement cell, wherein the measurement cell further comprises a working electrode,
carrying out a detection cycle comprising adhering the protein coated magnetic microparticles to the working electrode of the measurement cell by applying a magnetic field to the measurement cell and applying an excitation energy, thereby causing the marker to luminesce,
measuring the luminescence and thereby acquiring a measurement signal, and
generating an output signal being indicative of the presence of the analyte in the liquid sample using the measurement signal.

2. The method of claim 1, wherein extracting a portion of fluid from the receptacle employs a pipetting probe.

3. The method of claim 1, wherein acquiring a signal being indicative of the amount of fluid contained in the receptacle employs a capacitive method.

4. The method of claim 1, wherein determining the rotational frequency for the stirring unit comprises:
providing the first signal to a data processing unit, and
in response to providing the first signal to the data processing unit receiving from the data processing unit a second signal indicative of the rotational frequency based on the amount of fluid.

5. The method of claim 4, wherein the data processing unit comprises a table, the table comprising information indicative of which rotational frequency to use for a defined amount of fluid, wherein the data processing system in response to receiving the first signal looks up the table for the rotational frequency appropriate for the amount of fluid the first signal is indicative of and provides a second signal being indicative of the rotational frequency appropriate for the amount of fluid.

6. The method of claim 5, wherein the data comprised in the table is determined empirically.

7. The method of claim 1 and further comprising repeating the method for a second detecting of an analyte in the liquid sample, wherein the period of time for stirring the fluid comprising the protein coated microparticles is held constant for the second detecting.

8. The method of claim 1, wherein stirring is only conducted prior to extracting fluid from the receptacle.

9. The method of claim 1, wherein subsequent execution of the method steps is carried out with the reduced amount of fluid contained in the receptacle.

10. The method of claim 1, wherein the excitation energy is applied by applying electrical energy, radiation energy and/or chemical energy.

11. The method of claim 1, wherein the marker is configured to be capable of effecting electrochemiluminescence, and wherein an electrochemically active substance contributes to an electrochemiluminescence reaction with the marker resulting in the luminescence.

12. The method of claim 10, in which the incubating comprises carrying out a reaction sequence comprising at least one specific biochemical binding reaction to form a complex as a result of the presence of the analyte in the liquid sample, the complex comprising the marker and said complex further being bound to a magnetic microparticle,
said detection cycle comprising a capturing step during which the complex is contacted with the working electrode in such a manner that said microparticle is attracted by the magnetic field of a magnetic component positioned on the side of the working electrode facing away from the sample, thereby being deposited on the surface of said working electrode facing the sample, and applying a potential to the working electrode to trigger the electrochemiluminescence reaction of the marker with the electrochemically active substance causing the luminescence of the marker to thereby determine the presence of the analyte in the liquid sample.

13. The method of claim 1, wherein the luminescence is measured using an optical sensor, and wherein the measurement signal comprises an output signal of the optical sensor.

14. The method of claim 2, wherein the acquiring the first signal is conducted with a capacitive sensor located on the pipetting probe.

* * * * *